US009161943B2

(12) United States Patent
Lu et al.

(10) Patent No.: US 9,161,943 B2
(45) Date of Patent: Oct. 20, 2015

(54) SUSTAINED RELEASE COMPOSITION AND MANUFACTURING METHOD THEREOF

(75) Inventors: Jui-Mei Lu, Jhudong Township, Hsinchu County (TW); Chia-Wen Liu, Yangmei Township, Taoyuan County (TW); Po Hong Lai, Pingjhen (TW); John Jianghann Lin, Keelung (TW); Chiao Pin Li, Kaohsiung (TW); Sung En Chen, Kaohsiung Country (TW); Yo Wen Lo, Shueishang Township, Chiayi County (TW); Ming-Thau Sheu, Sijhih (TW); Min-Ying Lin, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 582 days.

(21) Appl. No.: 11/967,315

(22) Filed: Dec. 31, 2007

(65) Prior Publication Data

US 2009/0169632 A1 Jul. 2, 2009

(51) Int. Cl.
| A61K 31/70 | (2006.01) |
| A61K 9/00 | (2006.01) |
| A61K 9/16 | (2006.01) |
| A61K 9/50 | (2006.01) |
| A61K 31/7088 | (2006.01) |

(52) U.S. Cl.
CPC .............. *A61K 31/70* (2013.01); *A61K 9/0019* (2013.01); *A61K 9/1647* (2013.01); *A61K 9/5031* (2013.01); *A61K 31/7088* (2013.01)

(58) Field of Classification Search
CPC . A61K 31/70; A61K 31/7088; A61K 9/0019; A61K 9/1647; A61K 9/5031
See application file for complete search history.

(56) References Cited

U.S. PATENT DOCUMENTS

| 5,656,299 | A | 8/1997 | Kino et al. | |
| 2002/0009493 | A1 | 1/2002 | Schwendeman et al. | |
| 2004/0247870 | A1* | 12/2004 | Brown et al. | 428/402 |
| 2006/0228414 | A1 | 10/2006 | Cook | |
| 2007/0104778 | A1* | 5/2007 | Zeng et al. | 424/451 |
| 2007/0196416 | A1* | 8/2007 | Li et al. | 424/422 |
| 2008/0182909 | A1 | 7/2008 | Schwendeman et al. | |
| 2010/0112028 | A1* | 5/2010 | Hellerbrand et al. | 424/423 |

FOREIGN PATENT DOCUMENTS

| JP | 2001517685 | 10/2001 |
| JP | 2007500229 | 1/2007 |
| JP | 2007524645 | 8/2007 |
| JP | 2009155302 | 7/2009 |
| JP | 2009543849 | 12/2009 |
| WO | 9628143 | 9/1996 |
| WO | 9709985 | 3/1997 |
| WO | 2004089291 | 10/2004 |
| WO | 2005049090 | 6/2005 |
| WO | 2005070332 | 8/2005 |
| WO | WO 2005070332 A1 * | 8/2005 |
| WO | 2006036614 | 4/2006 |
| WO | 2008026894 | 3/2008 |

OTHER PUBLICATIONS

Mu et al, Vitamin E TPGS Used As an Emulsifier in the Solvent Evaporation/Extraction Technique for Fabrication of POlymeric Nanospheres for Controlled Release of Paclitaxel (Journal of Controlled Release 80 (2002) 129-144).*
Single et al, Paclitaxel and Its Formulations, International Journal of Pharmaceutics 235 (2002), 179-192.*
Mu, L.; Feng, S.S. "Vitamin E TPGS used as emulsifier in the solvent evaporation /extraction technique for fabrication of polymeric nanospheres for controlled release of paclitaxel (Taxol)" Journal of Controlled Release 80 (2002) 129-144.*
Diaz, R.V.; Soriano, I.; Delgado, A.; Llabres, M.; Evora, C. "Effect of surfactant agents on the release of 125I-bovine calcitonin from Plga microspheres: in vitro-in vivo study." Journal of Controlled Release 43 (1997) 59-64.*
Singla, A.K.; Garg, A.; Aggarwal, D. "Paclitaxel and its formulations" International Journal of Pharmaceutics 235 (2002) 179-192.*
Lutrol F-127 Product Sheet (http://www.innovate-excipients.basf.com/Products.aspx?PRD=30035120), accessed Jul. 18, 2013.*
Rongyi, L. "In Vitro Study of Anticancer Drug Doxorubicin in PLGA/PLA Based Microparticles" 2005, pp. 1-93.*
JP Office Action mailed Jan. 12, 2010.
English abstract of JP2007524645, pub. Aug. 30, 2007.
English abstract of JP2009543849, pub. Dec. 10, 2009.
"Effect of Surfactant Agents on the Release of 125I-bovine Calcitonin from PLGA microspheres: in vitro—in vivo study" R.V. Diaz et al., Journal of Controlled Release, Mar. 1996.
"Optimization of Formulation Variables for the Development of Long Acting Microspheres Based Depot Injection of Olanzapine" T. Nahata et al., Journal of Microencapsulation, Sep. 2008.
Chinese language office action dated Apr. 14, 2011.
Japanese language office action dated Oct. 23 2012.
English language translation of office action.
English language translation of abstract of JP 2001517685 (published Oct. 9, 2001).

(Continued)

*Primary Examiner* — Brian-Yong Kwon
*Assistant Examiner* — Andrew S Rosenthal
(74) *Attorney, Agent, or Firm* — McClure, Qualey & Rodack, LLP

(57) ABSTRACT

A sustained release composition comprising a polymer and manufacturing method thereof. The sustained release composition comprises a polymer, a bioactive agent, and a release rate determined agent, wherein the release rate determined agent is dispersed in the sustained release composition to control the release rate of the bioactive agent. The method comprises providing an oil phase comprising a bioactive agent, a polymer, and a release rate determined agent; providing an aqueous phase comprising a surfactant; mixing the oil phase with the aqueous phase to form the sustained release composition having a controlled release effect.

12 Claims, 1 Drawing Sheet

(56) References Cited

OTHER PUBLICATIONS

English language translation of abstract of JP 2007500229 (published Jan. 11, 2007).
English language translation of abstract of JP 2009155302 (published Jul. 16, 2009).
Taiwanese language office action dated Nov. 25, 2011.

Zhang, Z., et al.; "The Drug Encapsulation Efficiency, In Vitro Drug Release, Cellular Uptake and Cytotoxicity of Paclitaxel-Loaded Poly(lactide)-Tocopheryl Polyethylene Glycol Succinate Nanoparticles;" Biomaterials 27; 2006; pp. 4025-4033.
"Characteristics for Microspheres of Phosphotydalcholine/Polyactide-Co-Glycolide for Protein Delivery in Vitro Study;" and its English language abstract; pp. 1-12.

* cited by examiner

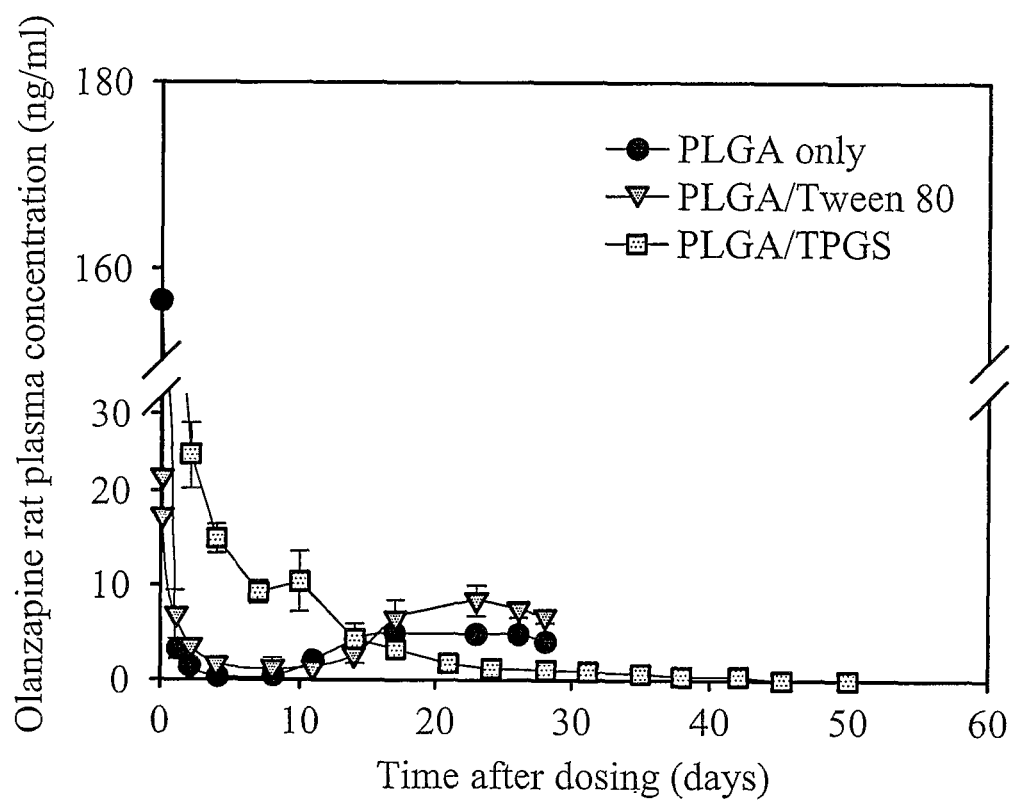

SUSTAINED RELEASE COMPOSITION AND MANUFACTURING METHOD THEREOF

BACKGROUND OF THE INVENTION

1. Field of the Invention

The present invention relates to a sustained release system, and in particular relates to a sustained release composition containing release rate determined agent.

2. Description of the Related Art

The desirability of coating medical devices such as, surgical implants, sutures and wound dressings with pharmaceutical agents is well known. Such coated devices provide a means for locally delivering pharmaceutical or therapeutic agents at the site of medical intervention to treat a variety of diseases. For example, surgical implants or sutures coated with antibiotics can provide local delivery of antibiotics directly to an implantation or suture site, thereby decreasing the onset of infection following the surgical intervention.

Thus, there is an increasing interest in developing a drug delivery system which is both safe and which provides a high biological availability of the drug, i.e. to maximize pharmaceutical activity of known drugs as well as to minimize the side effects thereof. Due to their uniform release rate during a given time period and the non-toxic property of degradation products, biodegradable polymers have been widely investigated as drug carriers. Biodegradable polymer drug carriers are especially useful for delivering drugs requiring continuous and sustained release with a single administration, e.g. peptide or protein drugs, which should be administered daily because of quick loss of activity in the body.

However, the traditional drug release curve includes three phases with an initial release phase, a lag phase, and a secondary release phase, wherein the drugs are only released at initial and secondary release phases. Thus, at the lag phase, it is necessary to combine an oral administration with the local administration to achieve a desired therapeutic goal, with the additional oral administration increasing costs and causing inconvenience. To overcome the above problems, a novel sustained release composition and manufacturing method thereof are needed.

BRIEF SUMMARY OF INVENTION

The invention provides a sustained release composition, comprising a polymer, a bioactive agent, and a release rate determined agent, wherein the bioactive and the release rate determined agent are dispersed in the sustained release composition, and the release rate determined agent controls a release rate of the bioactive agent.

The invention further provides a method for manufacturing a sustained release composition, comprising: providing an oil phase comprising a bioactive agent, a polymer, and release rate determined agent; providing an aqueous phase comprising a surfactant; mixing the oil phase with the aqueous phase to form the sustained release composition having a controlled release effect.

The invention further provides a method for treating an animal, comprising administering a pharmaceutically effective amount of the sustained release composition of the invention.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 1 shows the drug release curve of the sustained release compositions.

DETAILED DESCRIPTION OF INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a sustained release composition, comprising a polymer, a bioactive agent, and a release rate determined agent, wherein the bioactive and the release rate determined agent are dispersed in the sustained release composition, and the release rate determined agent controls a release rate of the bioactive agent.

The sustained release composition may contain one or more of the bioactive agents, which include nucleic acids, carbohydrates, peptides, proteins, small molecule pharmaceutical substances, immunogens, antineoplastic agents, or hormones. Examples of nucleic acids include, but are not limited to, DNAs, RNAs, chemically modified DNAs and chemically modified RNAs, aptamers, antisense oligonucleotides, RNA interferences, and small interfering RNAs. Examples of carbohydrates include, but are not limited to, heparin, low molecular weight heparin and the like. Examples of peptides include, but are not limited to, LHRH agonists and synthetic analogs, leuprolide, somatostatin analogs, hormones, octreotides, glucagons-like peptides, oxytocins and the like. Examples of proteins include, but are not limited to, antibodies, therapeutic proteins, human growth hormones (such as bone morphogenetic protein, TGF-$\beta$1, fibroblast growth factor, platelet-derived growth factor, or insulin-like growth factor), oxytocins, octreotides, gonadotropin-releasing hormones, leuprolide, interferons, insulin, calcitonin, interleukin, and the like. Examples of small molecule pharmaceutical substances include, but are not limited to, antiinfective agents (e.g. amphotericin B), cytotoxic agents, antihypertensive agents, antifungal agents (e.g. fluconazole, itraconazole, ketoconazole), antipsychotic agents (e.g. clozapine, olanzapine, risperidone, sertindole, aripiprazole, ziprasidone, or quetiapine), antidiabetic agents, immune stimulants (e.g. $\beta$-1,3/1,6-glucans), immune suppressants (e.g. cyclosporine, or prednisone), antibiotics (e.g. penicillin, cephalosprins, vancomycin hydrochloride, or lincomycin), antivirals, anticonvulsants, antihistamines, cardiovascular agents, anticoagulants, hormones, antimalarial, analgesics, anesthetics, steroids, nonsteroidal anti-inflammatories, and antiemetics. Examples of hormones include, but are not limited to, growth factor, melatonin, serotonin, thyroxin, triiodothyronine, epinephrine, norepinephrine, dopamine, adiponectin, angiotensinogen, cholecystokinin, erythropoietin, gastrin, glucagon, inhibin, secretin, thrombopoietin, or aldosterone. The bioactive agent can be present in the oil phase at a concentration of 0.1-10% by weight, preferably, 2% by weight.

The polymers dissolved in the solvent is a bio-molecule (biodegradable polymer), for example, phospholipids, lecithin, poly(lactiide)s, poly(glycolide)s, polylactide-co-glycolide (PLGA), polyglutamic acid, polycaprolactone (PCL), polyanhydrides, polyamino acid, polydioxanone, polyhydroxybutyrate, polyphophazenes, polyesterurethane, polycarbosyphenoxypropane-cosebacic acid, polycarbonates, polyesteramides, polyacetyls, polycyanoacrylates, polyetheresters, poly(alkylene alkylate)s, or copolymers thereof. The hydrophobic polymer can be degraded in the biological subject without impact.

TPGS (d-alpha-tocopheryl polyethylene glycol succinate) is commercially available from Eastman Chemical Company as "Vitamin E-TPGS". Vitamin E-TPGS is a water soluble derivative of natural source vitamin E, and similar to an amphiphile. In the invention, various chemical derivatives of vitamin E-TPGS including ester and ether linkages of various chemical moieties are included within the definition of vitamin E-TPGS. Rather, it is dispersed in the oil phase to control the release of the bioactive agent. According to an important feature of the invention, the drug release curve of the sustained release composition of the invention does not have a lag phase. Thus, the bioactive agent can be continuously released, which obviates the need for using additional oral administration. In the invention, TPGS is present in as amount of about 1 to 50% by weight of the total weight of the sustained release composition, preferably, 4 to 15% by weight.

In one embodiment, the sustained release composition is in form of a microparticle, microsphere, or microcapsule. Microsphere is typically approximately homogeneous in composition and microcapsules comprise a core of a composition distinct from a surrounding shell. For purposes of this disclosure, the terms microsphere, microparticle and microcapsule are used interchangeably. In another embodiment, the sustained release composition of the invention has a drug encapsulation rate exceeding 70%, preferably, 70% to 99.9%, a diameter exceeding 5 μm, preferably, 5 μm to 200 μm, most preferably 30 μm to 100 μm, and can continuously release the bioactive agent in the biological body in absence of the lag phase.

The sustained release compositions of the present invention can be applied systemically or topically. For example, the compositions can be administered by injection intramuscularly, intraperitoneally intravenously or subcutaneous. Additionally, the compositions can be in virtually any form, for example, lotions, ointments, creams, gels, drops, suppositories, sprays, liquids and powders. Conventional pharmaceutical carriers, aqueous, powder or oily bases, thickeners and the like may be incorporated.

The invention further provides a method for manufacturing a sustained release composition. The method comprises providing an oil phase; providing an aqueous phase comprising a surfactant; and mixing the oil phase with the aqueous phase to form a sustained release composition, wherein the oil phase contains a bioactive agent, a polymer, and a release rate determined agent.

As used herein, the term "oil phase" of the invention refers to the solution of the solvent, polymer, bioactive agent, and release rate determined agent, that will be mixed with an aqueous phase through emulsion process to provide the sustained release composition of the invention. The solvent of the oil phase includes, but are not limited to, methylene chloride, ethyl acetate, benzyl alcohol, acetone, acetic acid, propylene carbonate, dichloromethane, chloroform, 1,4-dioxane, dimethylformamide (DMF), dimethyl sulphoxide (DMSO), toluene, or tetrahydrofuran (THF).

The terms "release rate determined agent" of the invention refers to the solution of the surfactants which can control the release rate of the bioactive agent.

The release rate determined agent of the invention include, but are not limited to, Span® 80, Span® 85, oleic acid, PEG-PCL di-block copolymer, glyceryl tricaprylate, Pluronic® (F68), Tween® 80 or vitamin E-TPGS.

The terms "aqueous phase" refers to the solution of water and surfactants that is contacted with an oil phase through an emulsion process to provide the sustained release compositions of the present invention. The release rate determined agent are present at a concentration in the oil phase between 1 and 50% by weight. For example, they are present at a concentration between 4 to 15% by weight.

The surfactants of the invention include, but are not limited to, polyvinyl alcohol (PVA), NP-5, Triton X-100, Tween® 80, PEG 200-800, sodium dodecyl sulfate (SDS), alcohol ethoxylates, alkylphenol ethoxylates, secondary alcohol ethoxylates, fatty acid ester, or alkyl polyglycosides. The surfactants are present at a concentration in the aqueous between 0.1 and 10% by weight. For example, they are present at a concentration between 0.1 to 5% by weight.

In one embodiment, the oil phase is contacted with the aqueous phase to form an emulsion, wherein the emulsion comprises droplets of the oil phase dispersed in the aqueous phase. Solvent is subsequently removed from the emulsion droplets to form hardened microparticles. The solvent can be removed by evaporation, filtration, or extraction into an extraction liquid. For example, the extraction liquid may be water. The hardened microparticles may then be recovered from the aqueous phase and dried.

The emulsion is produced by stirring the organic and aqueous phases. In one embodiment, the emulsion is produced by use of a mixer, such as a static mixer. Alternatively, the emulsion is produced by use of turbulent mixing.

The emulsion process may be carried out at any temperature between the boiling point and freezing point of the components. In one embodiment, the temperature ranges from 0° C. to 100° C., or between about 5° C. to 75° C., or between about 15° C. and about 60° C.

Additionally, cosolvents may be added to the oil phase. They are optionally used to promote solubility of the bioactive agent in the oil phase. In one embodiment, they include, but are not limited to, dimethyl sulfoxide, dimethyl formamide, n-methylpyrrolidinone, PEG 200, PEG 400, methyl alcohol, ethyl alcohol, isopropyl alcohol, and benzyl alcohol. The cosolvent may be present between 0 and 90% by weight of the solvent of the oil phase, or between 0 and 50% by weight of the solvent of the oil phase. The bioactive agent may be dissolved first in an appropriate volume of the cosolvent which is then added to the solvent of the oil phase, optionally dissolved with the biodegradable polymer, so as to form a solution containing all the components of the oil phase. It should be noted that, a person of ordinary skill may adjust the volumes and order of addition to achieve the desired solution of bioactive agent and biodegradable polymer. In one embodiment, the bioactive agent will be present in the oil phase at a concentration of 0.1 to 10% by weight. In another embodiment, the biodegradable polymer will be present in the oil phase at a concentration of 0.1 to 20% by weight. For example, the biodegradable polymer will be present in the oil phase at a concentration of 1 to 10% by weight.

The invention further provides a method for treating an animal, comprising administering a pharmaceutically effective amount of the sustained release composition of the invention. The animal is not necessary to combine an oral administration with the local administration to improve treatment effects, because the sustained release composition can continuously release bioactive agent.

The sustained release compositions of the invention may be suspended in any aqueous solution or other diluent for injection in a human or animal patient in need of treatment. Aqueous diluent solutions may further include a viscosity enhancer selected from the group consisting of sodium carboxymethylcellulose, sucrose, mannitol, dextrose, trehalose and other biocompatible viscosity enhancing agents.

The "animal" of the invention refers as used herein refers to any animal of the class Mammalia. A mammalian animal of the invention includes, human or non-human mammal, e.g. a dog, a cat, a mouse, a rat, a cow, a sheep, a pig, a goat, or a primate, and expressly includes laboratory mammals, livestock, and domestic mammals. In one embodiment, the mammals may be a human; in others, the mammal may be a rodent, such as a mouse or a rat.

EXAMPLE

Example 1

50/50 PLGA Microspheres Contained 0, 7, 26, 42% Vitamin-E TPGS 80 mg of olanzapine, 200 mg PLGA (LA/GA ratio=50/50, M.W.=43000) and distinct amount vitamin E-TPGS (0, 7, 26, 42% by weight) were co-dissolved in 5 mL of dichloromethane to form an oil phase. The oil phase was dropped into 1000 mL of cooled aqueous phase containing 0.1% polyvinyl alcohol (PVA) and emulsified at 1000 rpm. The resulting o/w emulsion was agitated continuously for 3 h at room temperature. The microspheres were collected by centrifugation, washed with F68, water and freeze-dried. Then the microspheres were evaluated for particle size and drug encapsulated efficiency by Multisizer and High Performance Liquid Chromatography (HPLC). The results showed that the particle size were 68.4±28.3, 71.6±27.3, 91.0±35.8, 101.9±42.8 µm and the encapsulated efficiency were 77.7, 83.5, 85.9, 85.2% of the microspheres contained 0, 7, 26, 42% (w/w) vitamin E-TPGS, respectively.

Example 2

85/15 PLGA Microspheres Contained 0, 4, 15, 26% Vitamin E-TPGS 320 mg of olanzapine, 800 mg PLGA (LA/GA ratio=85/15, M.W.=53000) and distinct amount vitamin E-TPGS (0, 4, 15, 26% by weight) were co-dissolved in 15 mL of dichloromethane to form an oil phase. The oil phase was dropped into 2000 mL of cooled aqueous phase containing 0.1% polyvinyl alcohol (PVA) and emulsified at 1000 rpm. The methods of agitation, collection and analysis are as previously defined in Example 1. The results showed that the particle size were 40.0±21.3, 58.8±28.4, 47.4±21.4, 62.9±25.9 µm and the encapsulated efficiency were 77.2, 74.7, 87.6, 83.7% of the microspheres contained 0, 4, 15, 26% (w/w) vitamin E-TPGS, respectively.

Example 3

50/50 PLGA Microspheres Contained a Different Aqueous Phase 80 mg of olanzapine, 200 mg PLGA (LA/GA ratio=50/50, M.W.=43000) and 42% (w/w) of vitamin E-TPGS were co-dissolved in 5 mL of dichloromethane to form an oil phase. The oil phase was dropped into 1000 mL of a cooled aqueous phase and then emulsified at 1000 rpm, wherein the cooled aqueous phase included 0.05% PVA or 0.05% PVA containing 0.5% gelatin. The resulting o/w emulsion was agitated continuously for 3 h at room temperature. The microspheres were collected by centrifugation, washed with F68, water and free-dried. The analysis methods of the particle size and drug encapsulated efficiency are as previously defined above. The results showed that the particle size were 108.7±37.3, 85.5±31.4 µm and the encapsulated efficiency were 74.1, 73.1% of the microspheres contained 0.05% PVA without and with 0.5% gelatine, respectively.

Example 4

85/15 PLGA Microspheres Contained a Different Oil Phase 320 mg of olanzapine, 800 mg PLGA (LA/GA ratio=85/15, M.W.=43000) and 15 w/w % of vitamin E-TPGS were co-dissolved in 15 mL of dichloromethane to form an oil phase. In this Example, dichloromethane included pure dichloromethane (Formulation #1), dichloromethane containing ethanol (DCM:ethanol=2:1, Formulation #2), and dichloromethane containing acetone (DCM:acetone=2:1, Formulation #3), respectively. The oil phase was dropped into 2000 mL of cooled aqueous phase containing 0.1% PVA and emulsified at 1000 rpm. The methods of agitation, collection and analysis are as previously defined in Example 1. The results showed that the particle size were 76.2±31.4, 70.6±31.8, 70.6±31.8 µm and the encapsulated efficiency were 86.8, 89.7, 88.5% of the microspheres in the Formulation #1, #2, #3.

Example 5

85/15 PLGA Microspheres Contained a Different LA/GA Ratio 320 mg of olanzapine, 800 mg of PLGA and 15% (w/w) vitamin E-TPGS were co-dissolved in 15 mL of dichloromethane to form an oil phase, wherein the PLGA had a different LA/GA ratio, which included 85/15:50/50=3:1 (Formulation #1), 85/15:50/50=1:3 (Formulation #2), and 75/20:50/50=4:1 (Formulation #3), respectively. The oil phase was dropped into 2000 mL of cooled aqueous phase containing 0.1% PVA and emulsified at 1000 rpm. The methods of agitation, collection and analysis are as previously defined in Example 1. The results showed that the particle size were 62.2±32.0, 59.1±24.9, 41.1±19.1 µm and the encapsulated efficiency were 84.9, 84.2, 83.2% of the microspheres in the Formulation #1, #2, #3.

Example 6

75/25 PLGA Microspheres 320 mg of olanzapine, 800 mg PLGA (LA/GA ratio=75/25) and 4% (w/w) of vitamin E-TPGS were co-dissolved in 15 mL of dichloromethane to form an oil phase. In this Example, the molecule weight of the PLGA was 30000 Da. and 21000 Da., respectively. The oil phase was dropped into 2000 mL of cooled aqueous phase containing 0.1% PVA and emulsified at 1000 rpm. The methods of agitation, collection and analysis are as previously defined in Example 1. The results showed that the particle size were 43.5±18.8, 37.4±20.2 µm and the encapsulated efficiency were 80.8, 77.6% of the microspheres comprised of 30000, 21000 Da. PLGA, respectively.

Example 7

85/15 PLGA Microspheres 320 mg of olanzapine, 800 mg PLGA (LA/GA ratio=85/15) and 4% (w/w) of vitamin E-TPGS were co-dissolved in 15 mL of dichloromethane to form an oil phase. In this Example, the molecule weight of PLGA included 53000 and 27000 Da., respectively. The methods of agitation, collection and analysis are as previously defined in Example 1. The results showed that the particle size were 58.8±28.4, 43.9±20.6 μm and the encapsulated efficiency were 74.7, 77.0% of the microspheres comprised of 53000, 27000 Da. PLGA, respectively.

Example 8

Different Release Rate Determined Agents Formulations 320 mg of olanzapine, 800 mg PLGA (LA/GA ratio=85/15, M.W.=53000) and distinct release rate determined agent (Span® 80, Span® 85, oleic acid, PEG-PCL di-block copolymer, glyceryl tricaprylate, Pluronic®, Tween® 80) were co-dissolved in 15 mL of dichloromethane to form an oil phase. The oil phase was dropped into 2000 mL of cooled aqueous phase containing 0.1% polyvinyl alcohol (PVA) and emulsified at 1000 rpm. The methods of agitation, collection and analysis are as previously defined in Example 1. The results showed that the particle size were 46.7±18.6, 40.3±15.5, 46.3±22.6, 55.7±27.3, 49.5±22.0, 68.1±30.9, 30.1±14.9 μm and the encapsulated efficiency were 86.9, 78.2, 79.4, 87.2, 69.5, 85.2, 75.5% of the microspheres comprise distinct release rate determined agent, respectively.

Example 8

Drug Release In Vivo

Sprague-Dawley rats were selected for the evaluation of depot formulations because the size of their leg muscles facilitates dose administration and evaluation of the injection site.

The male Sprague-Dawley rats weight between 250 to 300 g. Rats were given a single injection with a 20- or 21-gauge needle into the biceps femoris. The dose volume varied with the concentration of the formulation but did not exceed 1 mL per injection. The rats were given 40 mg of olanzapine/kg body weight.

At each time point, a 0.1 mL blood sample was collected from the lateral tail vein into heparanized collection tubes. Blood samples were collected once prior to dose administration and at various time points after dose administration throughout the 50-day period. Typical time points are at 5 min, 10 min, 30 min, 1 hr, 2 hr, 4 hr, 6 hr, 1 d, 2 d, 4 d, 7 d, 10 d, 14 d, 17 d, 21 d, 24 d, 28 d, 31 d, 35 d, 38 d, 42 d, 45 d, 50 d after dose administration. Plasma was harvested and plasma concentration of olanzapine was determined by HPLC/MS-MS.

Microsphere containing 15% (w/w) vitamin E-TPGS prepared in Example 2, was administrated into rats by intramuscular injection. In the control groups, the TPGS of the microsphere was removed (PLGA only) or substituted for Tween 80 (PLGA/Tween 80). Referring to FIG. 1, microsphere containing TPGS continuously released olanzapine in the rats, and the drug release curve of microsphere did not have the lag phase.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A sustained release composition without lag phase comprising a polymer, a bioactive agent, and a release rate determined agent, wherein the bioactive agent and the release rate determined agent are dispersed in the sustained release composition, the release rate determined agent is vitamin E-TPGS present in amounts of 7%-42% by weight of the total weight of the sustained release composition for controlling the release rate of the bioactive agent,
   wherein the polymer is polylactide-co-glycolide (PLGA) and the bioactive agent is olanzapine, and
   wherein the sustained release composition is produced by an emulsion process comprising an oil phase including the bioactive agents, the polymer and the release rate determined agent before mixing with an aqueous phase.

2. The sustained release composition as claimed in claim 1, wherein the sustained release composition continually releases the bioactive agent.

3. The sustained release composition as claimed in claim 1, wherein the sustained release composition has an encapsulation rate of bioactive agent exceeding 70%.

4. The sustained release composition as claimed in claim 1, wherein the sustained release composition is a microsphere, microparticle, or microcapsule.

5. The sustained release composition as claimed in claim 4, wherein the microsphere, microparticle, or microcapsule has a diameter exceeding 5 μm.

6. The sustained release composition as claimed in claim 1, wherein the sustained release composition is used for intramuscular or subcutaneous injection.

7. A method for manufacturing a sustained release composition as claimed in claim 1, comprising:
   (a) providing an oil phase comprising olanzapine, polylactide-co-glycolide (PLGA), and vitamin E-TPGS;
   (b) providing an aqueous phase comprising a surfactant;
   (c) mixing the oil phase with the aqueous phase to form the sustained release composition; and
   (d) recovering the composition.

8. The method as claimed in claim 7, wherein the oil phase further comprises a solvent.

9. The method as claimed in claim 8, wherein the solvent comprises methylene chloride, ethyl acetate, benzyl alcohol, acetone, acetic acid, propylene carbonate, dichloromethane, chloroform, 1,4-dioxane, dimethylformamide (DMF), dimethyl sulphoxide (DMSO), toluene, or tetrahydrofuran (THF).

10. The method as claimed in claim 7, wherein the surfactant comprises polyvinyl alcohol (PVA), NP-5, Triton x-100, Tween 80, PEG 200-800, sodium dodecyl sulfate (SDS), alcohol ethoxylates, alkylphenol ethoxylates, secondary alcohol ethoxylates, fatty acid ester, or alkyl polyglycosides.

11. The method as claimed in claim 7, wherein the release rate determined agents has a final concentration of about 7 to 42% by weight.

12. The method as claimed in claim 7, wherein the sustained release composition is a microsphere, microparticle, or microcapsule.

* * * * *